(12) United States Patent
Sommer et al.

(10) Patent No.: US 10,035,009 B2
(45) Date of Patent: Jul. 31, 2018

(54) SYSTEMS AND METHODS FOR TREATING PANCREATIC CANCER

(71) Applicant: The Board of Trustees of the Leland Stanford Junior University, Palo Alto, CA (US)

(72) Inventors: Frank Graham Sommer, Stanford, CA (US); Chris J. Diederich, Novato, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 583 days.

(21) Appl. No.: 14/253,801

(22) Filed: Apr. 15, 2014

(65) Prior Publication Data
US 2015/0018725 A1   Jan. 15, 2015

Related U.S. Application Data

(60) Provisional application No. 61/812,126, filed on Apr. 15, 2013.

(51) Int. Cl.
| | |
|---|---|
| *A61H 1/00* | (2006.01) |
| *A61M 37/00* | (2006.01) |
| *A61N 7/02* | (2006.01) |
| *A61B 18/00* | (2006.01) |
| *A61N 7/00* | (2006.01) |
| *A61B 90/00* | (2016.01) |

(52) U.S. Cl.
CPC ......... *A61M 37/0092* (2013.01); *A61N 7/022* (2013.01); *A61B 2018/0022* (2013.01); *A61B 2018/00267* (2013.01); *A61B 2018/00285* (2013.01); *A61B 2018/00482* (2013.01); *A61B 2090/374* (2016.02); *A61N 2007/0078* (2013.01)

(58) Field of Classification Search
CPC .............................. A61N 7/00; A61H 23/0245
See application file for complete search history.

(56) References Cited

U.S. PATENT DOCUMENTS

| | | | |
|---|---|---|---|
| 4,327,738 A | 5/1982 | Green et al. | |
| 4,349,032 A | 9/1982 | Koyata | |
| 4,817,635 A | 4/1989 | Joines et al. | |
| 5,492,126 A * | 2/1996 | Hennige | A61B 8/12 600/439 |

(Continued)

FOREIGN PATENT DOCUMENTS

| | | |
|---|---|---|
| CN | 102122356 | 7/2011 |
| EP | 1142606 A2 | 10/2001 |

(Continued)

OTHER PUBLICATIONS

Elmar M. Merkle, et al, "MR Imaging-guided Radio-frequency Thermal Ablation in the Pancreas in a Porcine Model with a Modified Clinical C-Arm System1", Nov. 1999.

(Continued)

*Primary Examiner* — Hien Nguyen
(74) *Attorney, Agent, or Firm* — Vista IP Law Group, LLP (57) ABSTRACT

A method of treating pancreatic cancer includes: inserting a device into a stomach or a duodenum; securing at least a portion of the device in position relative to the stomach or the duodenum; and delivering ultrasonic energy from the device to treat a target site in a pancreas.

17 Claims, 9 Drawing Sheets

(56) References Cited

U.S. PATENT DOCUMENTS

| | | |
|---|---|---|
| 5,558,092 A | 9/1996 | Unger et al. |
| 5,762,066 A | 6/1998 | Law et al. |
| 6,139,819 A | 10/2000 | Unger et al. |
| 6,231,834 B1 | 5/2001 | Unger et al. |
| 6,428,504 B1 | 8/2002 | Riaziat et al. |
| 6,521,211 B1 | 2/2003 | Unger et al. |
| 6,575,969 B1 | 6/2003 | Rittman, III et al. |
| 6,589,174 B1 | 7/2003 | Chopra et al. |
| 6,788,977 B2 | 9/2004 | Fenn et al. |
| 7,179,449 B2 | 2/2007 | Lanza et al. |
| 7,198,778 B2 | 4/2007 | Achilefu et al. |
| 7,220,258 B2 | 5/2007 | Myhr |
| 7,329,402 B2 | 2/2008 | Unger et al. |
| 7,452,551 B1 | 11/2008 | Unger et al. |
| 7,514,069 B2 | 4/2009 | Achilefu et al. |
| 7,771,418 B2 | 8/2010 | Chopra et al. |
| 8,108,030 B2 | 1/2012 | Castella et al. |
| 8,162,834 B2 | 4/2012 | Feldman et al. |
| 2004/0002647 A1 | 1/2004 | Desai |
| 2004/0187876 A1 | 9/2004 | Myhr |
| 2004/0241095 A1 | 12/2004 | Achilefu et al. |
| 2006/0173442 A1 | 8/2006 | Dritschilo et al. |
| 2006/0182687 A1 | 8/2006 | Yang et al. |
| 2006/0293731 A1 | 12/2006 | Rubinsky et al. |
| 2007/0117133 A1 | 5/2007 | Trieu et al. |
| 2007/0167755 A1 | 7/2007 | Kolios et al. |
| 2007/0239062 A1 | 10/2007 | Chopra et al. |
| 2007/0255117 A1 | 11/2007 | Lanza et al. |
| 2007/0260138 A1 | 11/2007 | Feldman et al. |
| 2008/0015571 A1 | 1/2008 | Rubinsky et al. |
| 2008/0058316 A1 | 3/2008 | Eberhart et al. |
| 2008/0058788 A1 | 3/2008 | Boyden et al. |
| 2008/0154128 A1 | 6/2008 | Milner |
| 2008/0154344 A1 | 6/2008 | Trusty et al. |
| 2008/0177180 A1 | 7/2008 | Azhari et al. |
| 2009/0048546 A1 | 2/2009 | Appelman et al. |
| 2009/0069677 A1 | 3/2009 | Chen et al. |
| 2009/0143639 A1 | 6/2009 | Stark |
| 2009/0169478 A1 | 7/2009 | Leuschner et al. |
| 2009/0198131 A1 | 8/2009 | Fedewa et al. |
| 2009/0234225 A1 | 9/2009 | Martin et al. |
| 2009/0326359 A1 | 12/2009 | Hendriks et al. |
| 2010/0030190 A1 | 2/2010 | Singh |
| 2011/0034833 A1 | 2/2011 | Chopra et al. |
| 2011/0112400 A1* | 5/2011 | Emery ............... A61B 8/12 600/439 |
| 2011/0257523 A1* | 10/2011 | Hastings ........... A61B 8/0891 600/439 |
| 2012/0027727 A1 | 2/2012 | Hall et al. |
| 2012/0034227 A1 | 2/2012 | Arlen et al. |
| 2012/0059018 A1 | 3/2012 | Park et al. |
| 2012/0101370 A1 | 4/2012 | Razzaque et al. |
| 2012/0150031 A1 | 6/2012 | Castella et al. |
| 2014/0052224 A1* | 2/2014 | Kassab ............... A61F 7/123 607/105 |
| 2014/0163371 A1* | 6/2014 | Matsui ............... A61B 18/24 600/439 |

FOREIGN PATENT DOCUMENTS

| | | |
|---|---|---|
| EP | 0831932 B1 | 5/2004 |
| EP | 1444991 A1 | 8/2004 |
| EP | 1021197 B1 | 4/2007 |
| EP | 1847294 A1 | 10/2007 |
| EP | 2283869 A2 | 2/2011 |
| EP | 2305214 A1 | 4/2011 |
| EP | 2311398 A1 | 4/2011 |
| EP | 1854508 B1 | 5/2011 |
| EP | 2394580 A1 | 12/2011 |
| WO | WO8809152 A1 | 12/1988 |
| WO | WO9221023 A1 | 11/1992 |
| WO | WO9308876 A1 | 5/1993 |
| WO | WO9405993 A2 | 3/1994 |
| WO | WO9639079 A1 | 12/1996 |
| WO | WO9640285 A1 | 12/1996 |
| WO | WO9913919 A1 | 3/1999 |
| WO | WO9955244 A1 | 11/1999 |
| WO | WO 0045856 A2 | 8/2000 |
| WO | WO 0103770 A1 | 1/2001 |
| WO | WO 0113986 | 3/2001 |
| WO | WO 0236161 A2 | 5/2002 |
| WO | WO 02060524 A2 | 8/2002 |
| WO | WO 2004004709 A1 | 1/2004 |
| WO | WO 2004017830 A2 | 3/2004 |
| WO | WO 2004026098 A2 | 4/2004 |
| WO | WO 2004026098 A3 | 4/2004 |
| WO | WO 2004035110 A2 | 4/2004 |
| WO | WO 2004064914 A2 | 8/2004 |
| WO | WO 2005002671 A1 | 1/2005 |
| WO | WO 2005089813 A2 | 9/2005 |
| WO | WO 2006018837 A3 | 2/2006 |
| WO | WO 2006042186 A2 | 4/2006 |
| WO | WO 2006074272 A2 | 7/2006 |
| WO | WO 2007001747 A2 | 1/2007 |
| WO | WO 2007008700 A2 | 1/2007 |
| WO | WO 2007124458 A3 | 1/2007 |
| WO | WO 2007021621 A2 | 2/2007 |
| WO | WO 2007030571 A2 | 3/2007 |
| WO | WO 2007100895 A2 | 9/2007 |
| WO | WO 2007117572 A2 | 10/2007 |
| WO | WO 2007124458 A2 | 11/2007 |
| WO | WO 2008007355 A1 | 1/2008 |
| WO | WO 2008015599 A2 | 2/2008 |
| WO | WO 2008067079 A2 | 6/2008 |
| WO | WO 2008086219 A1 | 7/2008 |
| WO | WO 2009002492 A1 | 12/2008 |
| WO | WO 2009029215 A1 | 3/2009 |
| WO | WO 2009032949 A2 | 3/2009 |
| WO | WO 2009041910 A1 | 4/2009 |
| WO | WO 2009041912 A1 | 4/2009 |
| WO | WO 2009042637 A2 | 4/2009 |
| WO | WO 2009045478 A1 | 4/2009 |
| WO | WO 2009052481 A1 | 4/2009 |
| WO | WO 2009103741 A2 | 8/2009 |
| WO | WO 2009111273 A2 | 9/2009 |
| WO | WO 2009154963 A1 | 12/2009 |
| WO | WO 2010118387 A1 | 10/2010 |
| WO | WO 2011028698 A2 | 3/2011 |
| WO | WO 2011033390 A1 | 3/2011 |
| WO | WO 2011073725 A1 | 6/2011 |
| WO | WO 2011102904 A1 | 8/2011 |
| WO | WO 2011102905 A1 | 8/2011 |
| WO | WO 2011102906 A1 | 8/2011 |
| WO | WO 2011137114 A1 | 11/2011 |
| WO | WO 2011137441 A2 | 11/2011 |
| WO | WO 2012007567 | 1/2012 |
| WO | WO 2012009703 A2 | 1/2012 |
| WO | WO 2012012750 A1 | 1/2012 |
| WO | WO 2012033901 A2 | 3/2012 |
| WO | WO 2012047582 A2 | 4/2012 |

OTHER PUBLICATIONS

Correlation of MR Thermal Imaging to Actual Size of Ablation During Laser Ablation Therapy, http://www.bioportfolio.com/resources/trial/88203/Correlation-Of-Mr-Thermal-Imaging-To-Actual-Size-Of-Ablation-During-Laser.html, May 2008.

* cited by examiner

SYSTEMS AND METHODS FOR TREATING PANCREATIC CANCER

RELATED APPLICATION DATA

This application claims priority to and the benefit of U.S. Provisional Patent Application No. 61/812,126, filed on Apr. 15, 2013, the entire disclosure of which is expressly incorporated by reference herein.

GOVERNMENT'S RIGHTS

This invention was made with Government support under contract NIH CA137472 and NIH CA 159992 awarded by National Institutes of Health. The Government has certain rights in this invention.

FIELD

The field of the application relates to medical devices and procedures for treating pancreatic cancer.

BACKGROUND

Pancreatic cancer is the fourth leading cause of cancer mortality in the United States. The National Cancer Institute estimates that there were 43,920 new cases of pancreatic cancer and 37,390 patients died from the disease in 2012. Different types of treatments are available to patients with pancreatic cancer. While surgery is generally considered the best hope for cure of this disease, only 10 to 20% of patients with pancreatic cancer are surgical candidates. Radiation therapy and chemotherapy are two other common methods to treat pancreatic cancer. However, the particular biochemical and physiologic characteristics of pancreatic cancer appear to limit the effectiveness of these standard forms of therapy. Applicant of the subject application determines that it may be desirable to have a new device and method that provide minimally invasive form of treatment of cancer to the pancreas without the undesirable side effects of chemotherapy and radiation.

SUMMARY

A method of treating pancreatic cancer includes: inserting a device into a stomach or a duodenum; securing at least a portion of the device in position relative to the stomach or the duodenum; and delivering ultrasonic energy from the device to treat a target site in a pancreas.

Optionally, the ultrasonic energy is delivered through a wall of the stomach or through a wall of the duodenum.

Optionally, the method further includes: inserting a transducer through a wall of the stomach or through a wall of the duodenum into the pancreas; wherein the ultrasonic energy is delivered from within the pancreas to reach the target site in the pancreas.

Optionally, the at least a portion of the device comprises an anchor, and the act of securing the at least a portion of the device comprises engaging the anchor with the stomach or the duodenum.

Optionally, the anchor comprises an expandable member, and the act of engaging the anchor comprises expanding the expandable member.

Optionally, the expandable member comprises a balloon.

Optionally, the ultrasonic energy is delivered through the balloon.

Optionally, the device further comprises an additional balloon, wherein the ultrasonic energy is delivered through the additional balloon.

Optionally, the device comprises a first elongated member with a lumen, and a second elongated member disposed within the lumen of the first elongated member, the second elongated member comprising an energy source, and wherein the method further comprises moving the second elongated member relative to the first elongated member.

Optionally, the act of moving the second elongated member comprises translating the second elongated member relative to the first elongated member, rotating the second elongated member relative to the first elongated member, or both.

Optionally, the ultrasonic energy is delivered from the device to create heat, hyperthermia, or thermal ablation, at the target site.

Optionally, the ultrasonic energy is delivered to release or deliver a drug to the target site in the pancreas.

Optionally, the ultrasonic energy is delivered to create mechanical perturbations at the target site in the pancreas.

Optionally, the device comprises a plurality of energy delivery components that are spaced apart from each other, and wherein the act of delivering the ultrasonic energy comprises selectively activating one or more of the plurality of energy delivery components.

Optionally, the energy delivery components are spaced apart from each other along a longitudinal axis of the device.

Optionally, the energy delivery components are spaced apart from each other along a circumference of the device.

Optionally, the method further comprises monitoring a thermal therapy process for the target site using a sensor that senses a characteristic of the target site.

A method of treating pancreatic cancer includes: inserting a device into a stomach or a duodenum, the device having a first elongated member with a lumen, a second elongated member disposed in the lumen of the first elongated member, and an energy source at the second elongated member; securing at least a portion of the device in position relative to the stomach or the duodenum; changing a relative position between the first elongated member and the second elongated member; and delivering ultrasonic energy from the energy source of the device to treat a target site in a pancreas.

Optionally, the ultrasonic energy is delivered through a wall of the stomach or through a wall of the duodenum.

Optionally, the method further includes: inserting the energy source through a wall of the stomach or through a wall of the duodenum into the pancreas; wherein the ultrasonic energy is delivered from within the pancreas to reach the target site in the pancreas.

Optionally, the at least a portion of the device comprises an anchor, and the act of securing the at least a portion of the device comprises engaging the anchor with the stomach or the duodenum.

Optionally, the anchor comprises an expandable member, and the act of engaging the anchor comprises expanding the expandable member.

Optionally, the expandable member comprises a balloon.

Optionally, the ultrasonic energy is delivered through the balloon.

Optionally, the device further comprises an additional balloon, wherein the ultrasonic energy is delivered through the additional balloon.

Optionally, the act of changing the relative position comprises translating the second elongated member relative to the first elongated member, rotating the second elongated member relative to the first elongated member, or both.

Optionally, the ultrasonic energy is delivered to create heat, hyperthermia, or thermal ablation, at the target site in the pancreas.

Optionally, the ultrasonic energy is delivered to release or deliver a drug to the target site in the pancreas.

Optionally, the ultrasonic energy is delivered to create mechanical perturbations at the target site in the pancreas.

Optionally, the energy source comprises a plurality of energy delivery components that are spaced apart from each other, and wherein the act of delivering the ultrasonic energy comprises selectively activating one or more of the plurality of energy delivery components.

Optionally, the energy delivery components are spaced apart from each other along a longitudinal axis of the device.

Optionally, the energy delivery components are spaced apart from each other along a circumference of the device.

Optionally, the method further includes monitoring a thermal therapy process for the target site using thermal imaging.

An apparatus for treating pancreatic cancer includes: a first elongated member having a distal end, a proximal end, a body extending between the distal end and the proximal end, and a lumen in the body, the first elongated member being flexible and being sized for insertion into a stomach or a duodenum; a securing mechanism at the distal end of the first elongated member, the securing mechanism configured for securing a portion of the first elongated member in position relative to surrounding tissue at the stomach or the duodenum; a second elongated member disposed within the lumen of the first elongated member, wherein the second elongated member is moveable relative to the first elongated member; and a transducer assembly at the second elongated member for delivering ultrasonic energy at an energy level sufficient to treat a target area in a pancreas.

Optionally, the securing mechanism comprises an expandable member.

Optionally, the expandable member comprises a balloon.

Optionally, the expandable member comprises a structural mesh.

Optionally, the apparatus further includes a fluid source to expand the securing mechanism.

Optionally, the second elongated member is translatable, rotatable, or both translatable and rotatable, relative to the first elongated member.

Optionally, the second elongated member is translatable out of an opening at the first elongated member, and wherein the transducer assembly is configured to deliver the ultrasonic energy from within the pancreas to the target area in the pancreas.

Optionally, the apparatus further includes an expandable member for transmitting the ultrasonic energy from the transducer assembly to the target area.

Optionally, the transducer assembly comprises two or more energy delivery components arranged in series along a longitudinal axis of the second elongated member.

Optionally, the transducer assembly comprises two or more energy delivery components arranged around a longitudinal axis of the second elongated member.

Optionally, the transducer assembly comprises multiple energy delivery components arranged both along and around a longitudinal axis of the second elongated member.

Optionally, the transducer assembly comprises a plurality of energy delivery components, and the apparatus further comprises a user interface for allowing a user of the apparatus to selectively activate one or more of the energy delivery components, and/or to adjust an amount of energy being delivered by the one or more of the energy delivery components.

Optionally, the apparatus further includes a delivery tube for accommodating the first elongated member, wherein the delivery tube is moveable relative to the first elongated member.

Optionally, the apparatus further includes a steering mechanism for bending the distal end of the first elongated member.

Optionally, the transducer assembly is configured for delivering ultrasonic energy to create heat, hyperthermia, or thermal ablation, at the target area.

Optionally, the transducer assembly is configured for delivering ultrasonic energy to release or deliver a drug at the target area.

Optionally, the transducer assembly is configured for delivering ultrasonic energy to generate mechanical perturbations in the target area.

Optionally, the apparatus further includes an imaging device coupled to the first elongate member or the second elongate member.

Optionally, the imaging device comprises an ultrasound imaging device.

Optionally, the imaging device comprises a coil for MR imaging.

Optionally, the imaging device is alongside the transducer assembly, is embedded in the transducer assembly, or is located at a center of the transducer assembly.

Other and further aspects and features will be evident from reading the following detailed description of the embodiments.

DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only exemplary embodiments and are not therefore to be considered limiting in the scope of the claims.

DETAILED DESCRIPTION OF THE EMBODIMENTS

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Figure 1A:
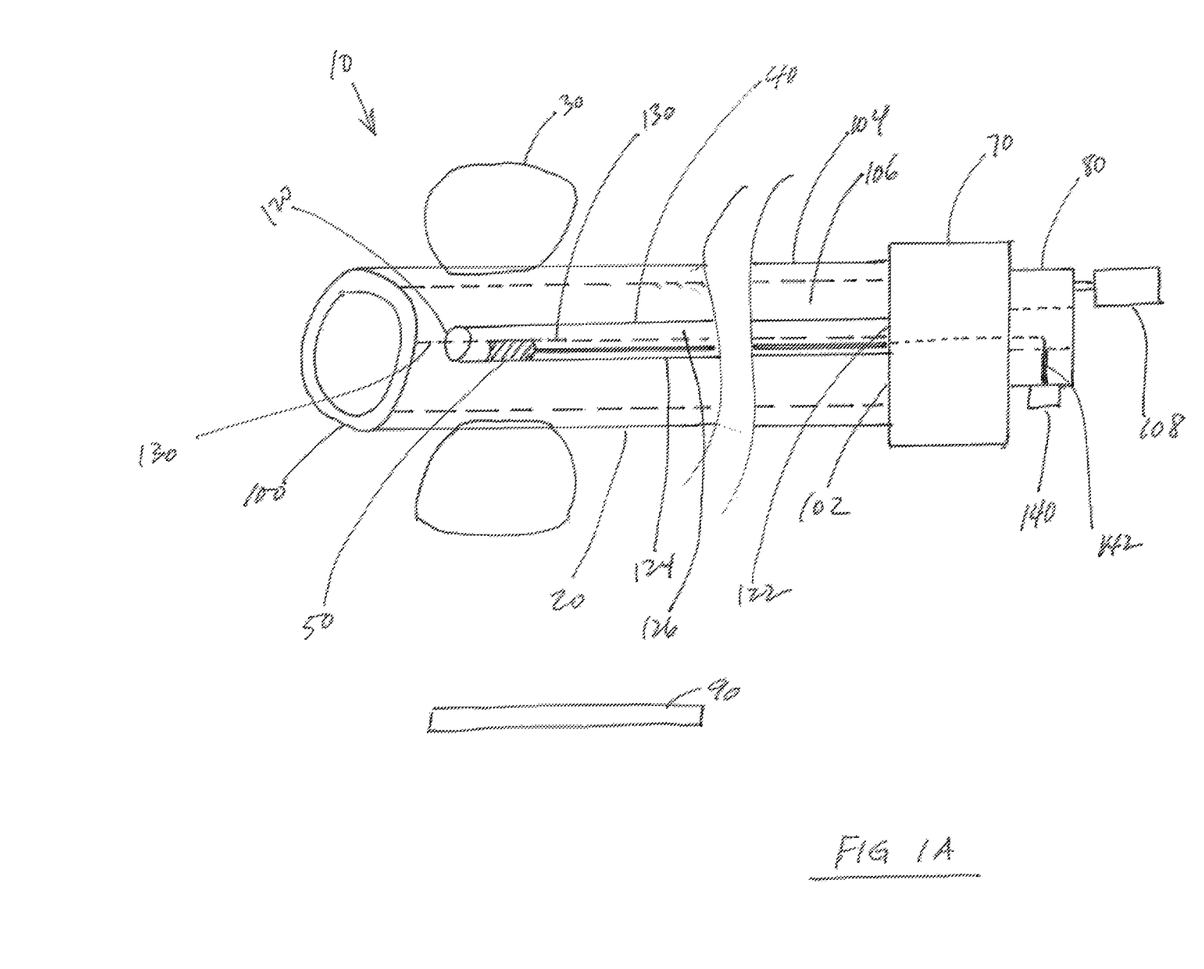
FIG. 1A illustrates a device for treating pancreatic cancer in accordance with some embodiments.

FIG. 1A illustrates a device 10 for treating pancreatic cancer in accordance with some embodiments.

The device 10 includes a first elongated member 20, a securing mechanism 30, a second elongated member 40, and a transducer 50. The device 10 also includes a first handle 70 coupled to the first elongated member 20, and a second handle 80 coupled to the second elongated member 40. The device 10 may be used with a thermal imaging device 90 for purpose of monitoring extent of the heating of the target tissue during a treatment procedure. In other embodiments, the thermal imaging device 90 may be a part of the device 10.

The first elongated member 20 includes a distal end 100, a proximal end 102, a body 104 extending between the distal end 100 and the proximal end 102, and a lumen 106 in the body 104. In the illustrated embodiments, the first elongated member 20 is flexible. In other embodiments, the first elongated member 20 may be rigid. Also, in the illustrated embodiments, the first elongated member 20 is sized for insertion into the stomach or duodenum. The first elongated member 20 may also have a length that allows the distal end 100 of the first elongated member 20 to reach the stomach or the duodenum through the mouth and the esophagus, while the proximal end 102 of the first elongated member 20 remains outside the patient.

Figure 1B:
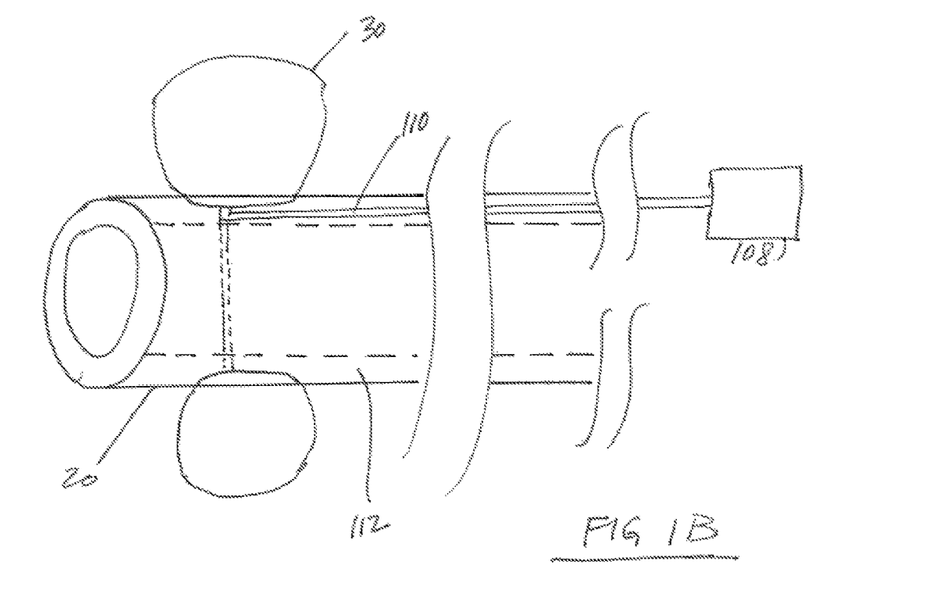
FIG. 1B is an enlarged view of a component of the device of FIG. 1A in accordance with some embodiments.
Figure 1C:
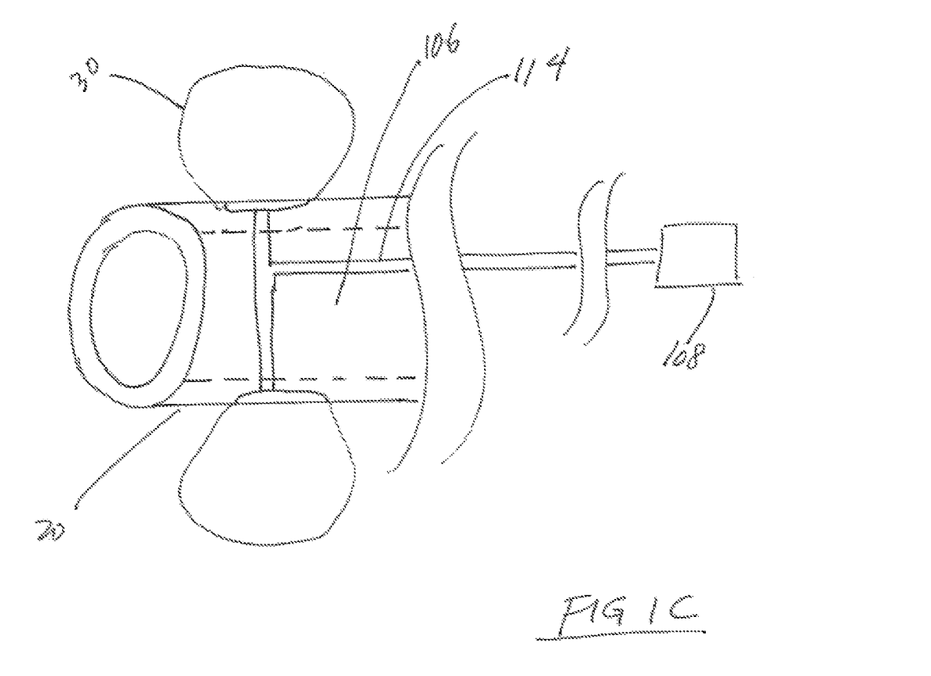
FIG. 1C is an enlarged view of a component of the device of FIG. 1A in accordance with some embodiments.

In the illustrated embodiment, the securing mechanism 30 is an expandable member. For example, the expandable member 30 may be a balloon in some embodiment, or a structural mesh in other embodiment. The securing mechanism 30 may have a first configuration with a low profile for allowing the securing mechanism 30 to be inserted through a delivery tract to reach a target site, and a second configuration with an expanded profile for allowing the securing mechanism 30 to engage tissue for securing the distal end 100 of the first elongated member 20 relative to tissue at the target site (e.g., stomach, duodenum, etc.). For example, in the embodiments in which the securing mechanism 30 is an expandable balloon, the expandable balloon may have an un-inflated configuration so that the balloon assumes a low profile for delivery to the target site. When the balloon reaches the target site, the balloon may be inflated to expand to engage tissue at the target site. The expanded balloon may have a size that is sufficiently large, so that the expanded balloon can engage with, and press against, the wall of the stomach or the duodenum, thereby allowing the balloon to function as an anchor to secure the distal end 100 of the first elongated member 20 relative to the wall of the stomach or the duodenum. In order to inflate the balloon, the device 10 is configured to be coupled to a fluid source 108 which may include a pump (e.g., syringe) that has the ability to deliver fluid into the balloon and also to apply suction to remove the fluid from inside the balloon to deflate the balloon once the procedure is completed. FIG. 1B and FIG. 1C illustrate how the fluid may be delivered to inflate the balloon. In some embodiments, the fluid may be delivered through a channel 110 in the wall 112 of the first elongated member 20 (FIG. 1B). In other embodiments, the fluid may be delivered to the balloon 30 using a tube 114 housed inside the first elongated member 20 (FIG. 1C).

In the illustrated embodiments of FIG. 1A, the second elongated member 40 is moveable relative to, and is within, the first elongated member 20. For example, the second elongated member 40 may be translatable relative to the first elongated member 20, rotatable relative to the first elongated member 20, or both. The second elongated member 40 has a distal end 120, a proximal end 122, a body 124 extending between the distal end 120 and the proximal end 122, and lumen 126 in the body 124. Similar to the first elongated member 20, the second elongated member 40 may have a length that allows the distal end 120 of the second elongated member 40 to reach the stomach or the duodenum through the mouth and the esophagus, while the proximal end 122 of the second elongated member 40 remains outside the patient.

As shown in the figure, the first handle 70 is secured to the proximal end 102 of the first elongated member 20, and the second handle 80 is secured to the proximal end 122 of the second elongated member 40. Movement of the second elongated member 40 relative to the first elongated member 20 may be achieved by manipulating the first handle 70, the second handle 80, or both. For example, in some embodiments, the second handle 80 may be axially translated (along a longitudinal axis 130) relative to the first handle 70 to translate the second elongated member 40 relative to the first elongated member 20. In other embodiments, the second handle 80 may be rotated about the axis 130 relative to the first handle 70 to rotate the second elongated member 40 relative to the first elongated member 20. In further embodiments, the second handle 80 may be both translated and rotated relative to the first handle 70.

In the illustrated embodiments, the act of moving the first elongated member 20 and/or the second elongated member 40 to change a relative position between the first and second elongated members 20, 40 may be accomplished manually by hand(s). In other embodiments, the act of moving the first elongated member 20 and/or the second elongated member 40 to change a relative position between the first and second elongated members 20, 40 may be accomplished automatically and mechanically using a positioning device.

As shown in the figure, the device 10 includes one transducer 50. The transducer 50 may be a single focused piezoelectric element in some embodiments. The transducer 50 is located on the distal end 120 of the second elongated member 40. The transducer 50 is configured to deliver ultrasonic energy towards target tissue at the pancreas to treat tumor(s) at the pancreas. In some embodiments, the transducer 50 is configured to deliver sufficient acoustic energy to raise the temperature of targeted tissue to a temperature that is anywhere from 50° C. to 60° C. In other embodiments, the transducer 50 may be configured to deliver sufficient acoustic energy to raise the temperature of targeted tissue to a temperature higher than 60° C.

In the illustrated embodiments, the device 100 also includes a control (e.g., one or more buttons, knobs, switches, touch screen, etc.) 140 on the second handle 80 and an electrical wire 142. The electrical wire 142 is coupled to the control 140 and the transducer 50 for purpose of transmitting signal to activate the transducer 50 in response to actuation of control 140. In other embodiments, the device 10 may include multiple energy delivery components (e.g., multiple transducers 50). Also, in some embodiments, the control 140 may allow one or more operation parameters (e.g., power level, phase, activation duration, etc.) for the transducer(s) 50 be configured to adjust an amount of energy being delivered by one or more of the energy delivery components 50. In the illustrated embodiments, the transducer 50 is on one side of second elongated member 40. In other embodiments, the transducer 50 may extend circumferentially around the second elongated member 40. The second elongated member 40 may be translated, rotated, or both, to aim at target tissue.

In some embodiments, in addition to being able to deliver treatment energy, the transducer 50 may also be configured to deliver energy for imaging purpose. The imaging may be used for guidance of the device 10, and/or monitoring thermal tissue changes during or after treatment. In other embodiments, instead of using the transducer 50 in the transducer assembly for imaging purpose, the device 10 may include another transducer solely for imaging purpose. Such imaging transducer may be located next to or alongside (e.g., within 5 cm from) the transducer 50. Also, in some embodiments, the imaging transducer and the transducer 50 may be axially aligned along the longitudinal axis of the device 10. In other embodiments, the imaging transducer may be embedded in the transducer 50. In further embodiments, the imaging transducer may be located at a center of the transducer 50.

In other embodiments, the device 10 may include more than one transducer 50. For example, the transducers 50 may be arranged in the manners shown in FIGS. 2A, 2B, and 2C.

Figure 2A:
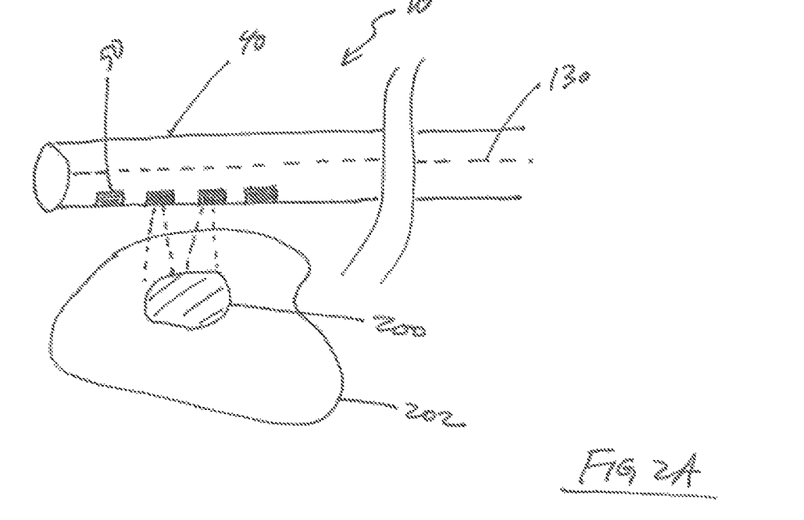
FIG. 2A illustrates a distal end of a component of the device of FIG. 1A in accordance with some embodiments.

FIG. 2A illustrates a device 10 which includes two or more transducers 50 arranged in series along the longitudinal axis 130 of the second elongated member 40. This configuration allows certain one(s) of the transducers 50 along the axis 130 to emit energy to target area 200 in the pancreas 202 without the need to translate the second elongated member 40 in a forward or backward fashion. For example, as shown in the figure, the target area 200 may be treated by certain one(s) (e.g., the middle two) of the transducers 50 that are aligned next to the target area 200 in the pancreas 202. Thus, those transducers 50 may be selectively activated to deliver energy to the target area 200. The second elongated member 40 may be rotated to aim at the target area 200 by moving the transducers 50 to a position facing the target area 200. The second elongated member 40 may also be translated to cover the target area 200 if the longitudinal extent of the target area 200 is greater than the length covered by the transducers 50. Also, in some embodiments, the second elongated member 40 may be rotated around the axis 130 to aim the transducers 50 towards the target area 200, and/or to sweep the energy transversely to cover a cross sectional width of the target area 200 (if the transverse extent of the target area 200 is greater than the length covered by the transducers 50).

Figure 2B:
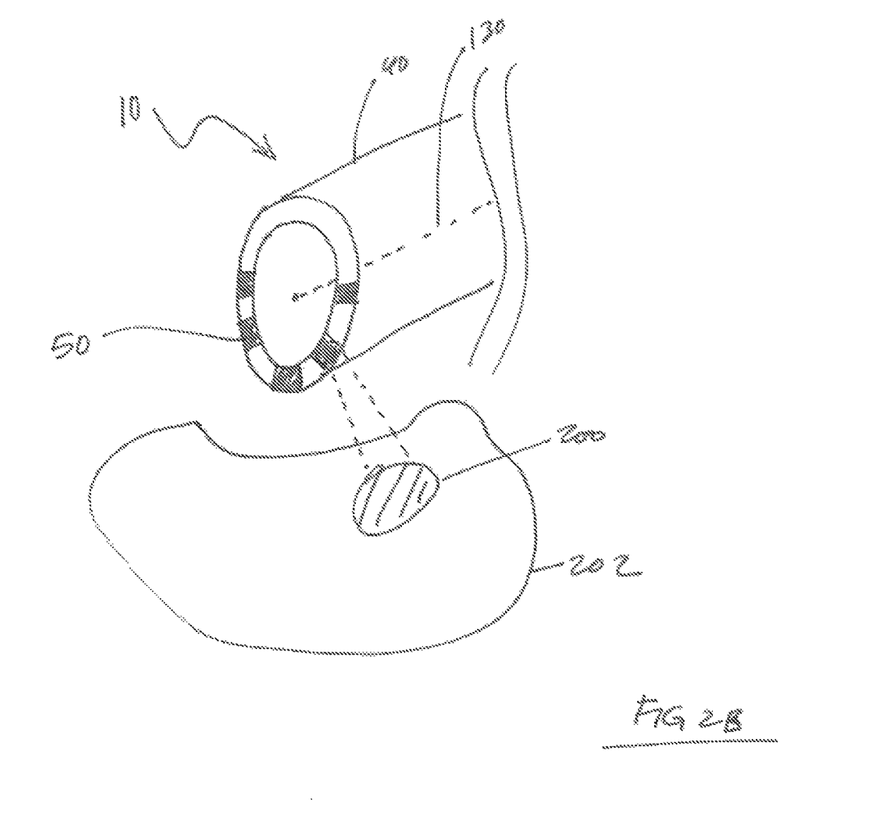
FIG. 2B illustrates a distal end of a component of the device of FIG. 1A in accordance with some embodiments.

In other embodiments, instead of arranging the transducers 50 along the longitudinal axis 130, the transducers 50 may be arranged circumferentially around the longitudinal axis 130. FIG. 2B illustrates a cross sectional view of device 10 which includes two or more transducers 50 arranged in a circumferential fashion around the longitudinal axis 130 of the second elongated member 40. This configuration allows certain one(s) of the transducers 50 around the axis 130 to emit energy to the target area 200 without the need to rotate the second elongated member 40. For example, as shown in the figure, the target area 200 is located on one side of the device 10. In such cases, one of the transducers 50 that is facing towards the target area 200 may be selectively activated to deliver energy to the target area 200. The second elongated member 40 may also be translated along the axis 130 to align the selected one of the transducers 50 to aim at the target area 200, and/or to sweep the energy longitudinally to cover a longitudinal length of the target area 200 (if the longitudinal extent of the target area 200 is greater than the length covered by the transducers 50).

Figure 2C:
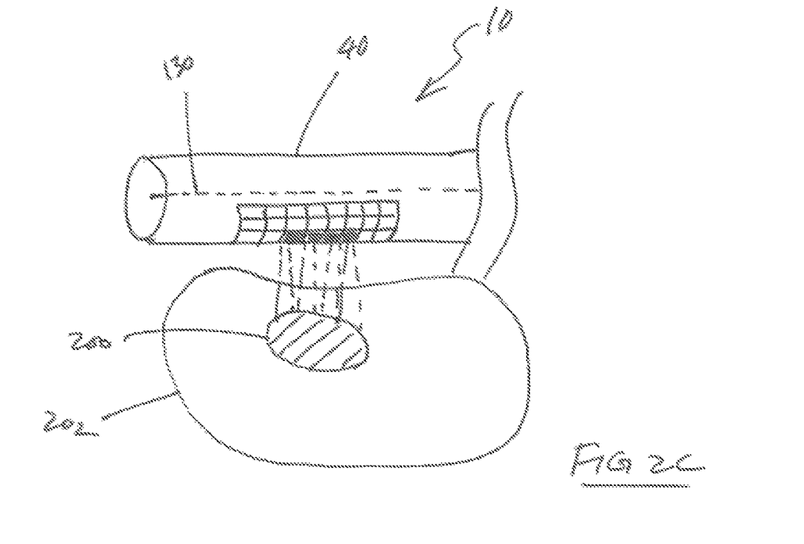
FIG. 2C illustrates a distal end of a component of the device of FIG. 1A in accordance with some embodiments.

In other embodiments, instead of arranging the transducers 50 (example of energy delivery components) along the longitudinal axis 130 or circumferentially around the longitudinal axis 130, the transducers 50 may be arranged both along the axis 130 and around the axis 130 to form an array of energy delivery components. FIG. 2C illustrates a device 10 which includes multiple transducers 50 arranged as a grid. The transducers 50 may be considered as transducer elements that are parts of a transducer assembly. This configuration allows certain one(s) of the transducers 50 to selectively emit energy to the target area 200 without the need to translate or rotate the second elongated member 40. For example, as shown in FIG. 2C, the target area 200 may be treated by certain one(s) of the transducers 50 that are aligned next to the target area 200 in the pancreas 202 and facing towards the target area 200. In such cases, those transducers 50 may be selectively activated to deliver energy to the target area 200. This configuration may also be used to deliver energy to multiple target areas 200 at the same time. When there are more than one target area 200 in the pancreas 202, several one(s) of the transducers 50 may be activated simultaneously to emit energy to the target areas at the same time. In addition, the second elongated member 40 may be translated to cover the target area 200 if the longitudinal extent of the target area 200 is greater than the length covered by the transducers 50. Alternatively or additionally, the second elongated member 40 may be rotated to cover the target area 200 if the cross sectional width of the target area 200 is greater than a circumferential range of the energy from the transducers 50. In the illustrated embodiments, the transducers 50 abut against each other. In other embodiments, the transducers 50 in the array may be spaced away from each other. Also, in some embodiments, the transducers 50 may collectively form a phased array.

In some embodiments, one or more of the transducers 50 in the embodiments of FIGS. 2A-2C may be configured to deliver treatment energy, while other one or more of the transducers 50 may be configured to deliver energy for imaging purpose. For example, a transducer 50 may be configured to deliver acoustic energy, and the same transducer 50 or another transducer 50 may be configured to detect acoustic energy reflected from tissue in the patient. The detected acoustic energy is converted into signals, and are then processed by a processor to determine an image of the tissue in the patient. This imaging can be used to guide the device 10, and/or to differentiate tissue changes during or after therapy that can be applied to monitor the therapy. In other embodiments, instead of using the transducers 50 in the transducer assembly for imaging purpose, the device 10 may include another transducer solely for imaging purpose. Such imaging transducer may be located next to or alongside (e.g., within 5 cm from) the transducers 50. In other embodiments, the imaging transducer may be embedded in the transducer assembly that comprises the transducer 50. In further embodiments, the imaging transducer may be located at a center of the transducer assembly.

A method of treating pancreatic cancer using the device 10 of FIG. 1 will now be described.

Figure 3A:
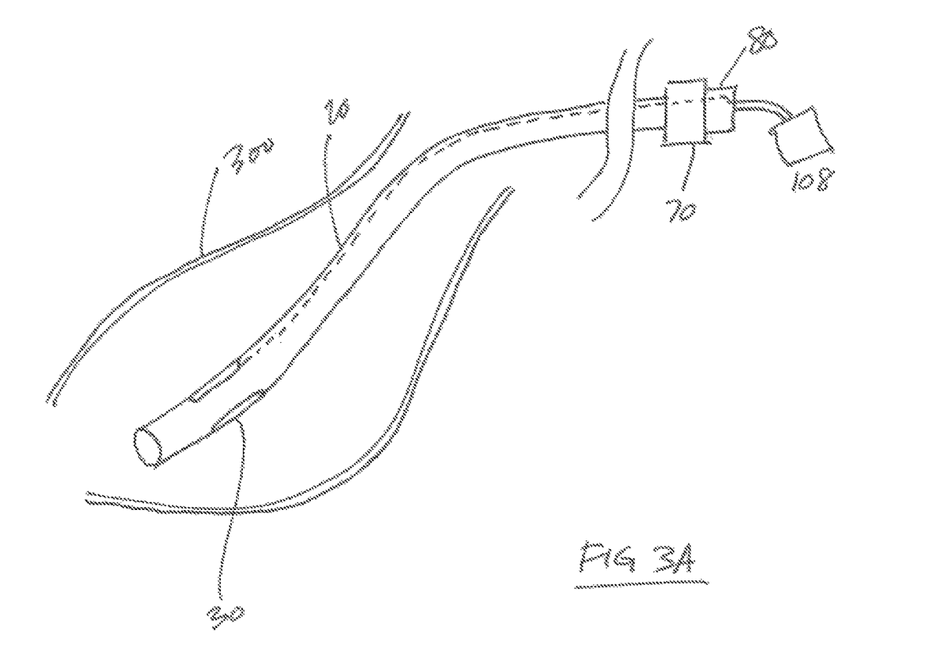
FIGS. 3A-3C illustrate a process for using the device of FIG. 1A in accordance with some embodiments.
Figure 3B:
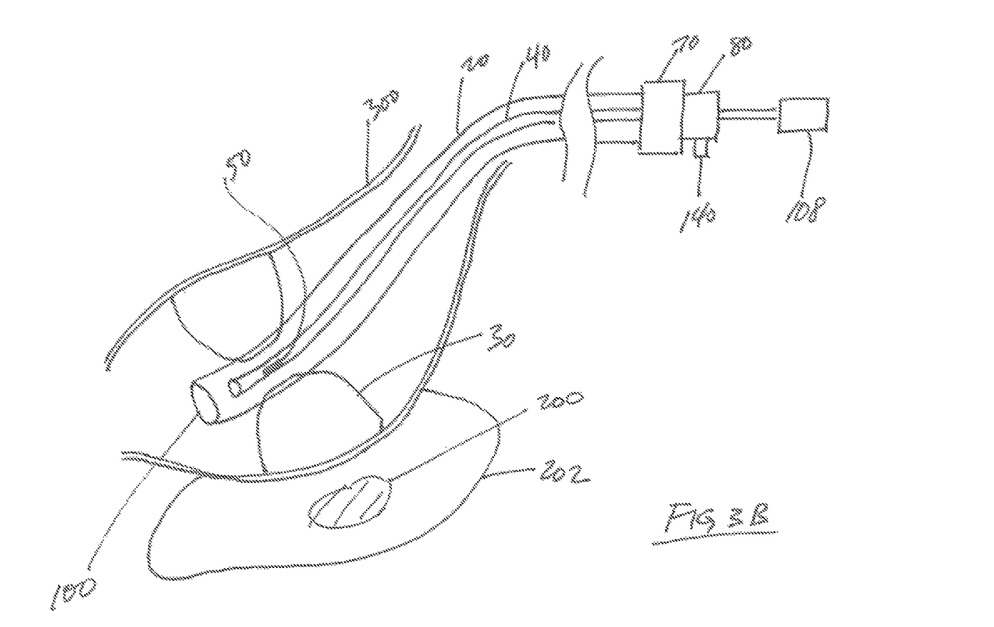
Figure 3C:
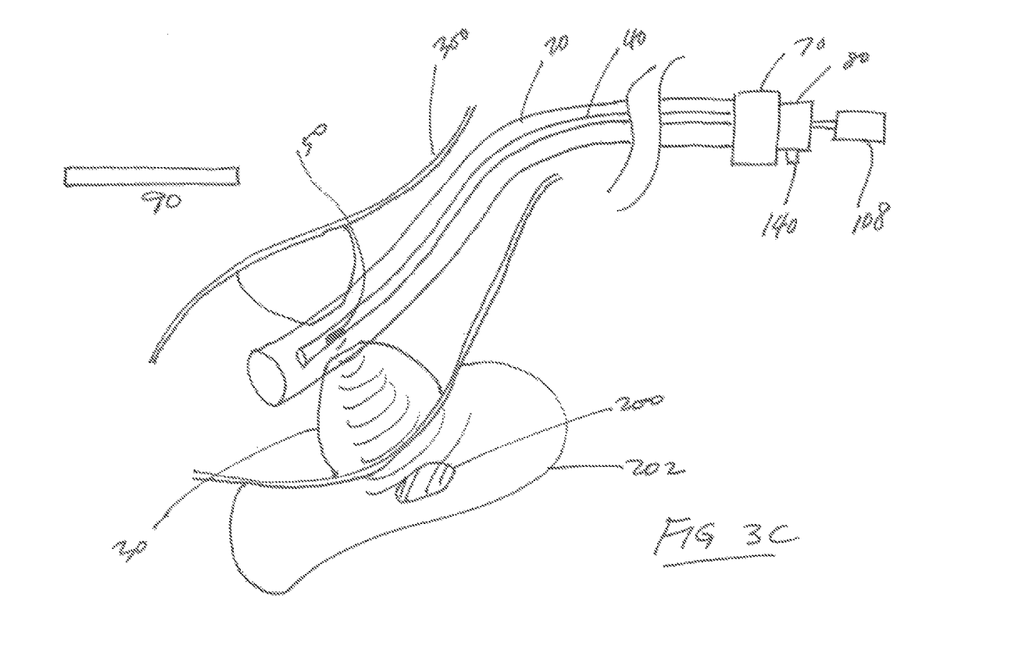

FIGS. 3A-3C illustrate a method of treating pancreatic cancer using the device 10 of FIG. 1 in accordance with some embodiments. The method will be described with reference the securing mechanism 30 being a balloon. However, it should be understood that the securing mechanism 30 may be a mesh, or other types of anchoring devices for securing itself relative to tissue.

As shown in FIG. 3A, the first elongated member 20 is first inserted through the mouth and is manipulated to pass through the esophagus into a desired position in the stomach or duodenum 300. Handle 70 may be used to manipulate the position of the first elongated member 20.

As shown in FIG. 3B, once the balloon 30 reaches the target site, the fluid source 108 is activated to deliver fluid to the balloon 30 and inflate the balloon to a size such that it presses against the interior wall (e.g., at least 2 wall portions) of the stomach or the duodenum 300, thereby allowing the balloon to function as an anchor to secure the distal end 100 of the first elongated member 20 relative to the wall of the stomach or the duodenum 300. In some embodiments, the fluid may be delivered through channel 110 in the wall 112 of the first elongated member 20 (like that shown in FIG. 1B). In other embodiments, the fluid may be delivered using a tube 114 (that provides a channel) housed inside the first elongated member 20 (like that shown in FIG. 1C). In the case where the fluid source 108 is a pump, the user turns on the pump for delivering fluid to the balloon 30. In the case where the fluid source 108 is a syringe, the user applies pressure to the syringe for delivering fluid to the balloon.

In the illustrated embodiments, the first elongated member 20 and second elongated member 40 are inserted together. In other embodiments, the first elongated member 20 may be inserted first, after which the second elongated member 40 is then inserted.

After the second elongated member 40 has been inserted, the handle 80 may be used to place the second elongated member 40 in a desired operative position which allows the transducer(s) 50 to deliver ultrasonic energy to the target area 200 at the pancreas 202. For example, the second elongated member 40 may be translated axially to align the transducer 50 with the target area 200 and/or rotated to face the transducer 50 towards the target area 200.

Next, as shown in FIG. 3C, once the second elongated member 40 is in a desirable position, the control 140 is operated to activate the transducer 50. In the embodiments where there are multiple transducers 50, the user may use the control 140 to selectively activate one or more of the transducers 50 and/or to change one or more parameters (e.g., power level, phase, activation time, etc.) for the transducer(s) 50 to adjust the energy being delivered by the one or more of the transducers 50.

In some cases, if the device 10 has a single transducer 50, the single transducer 50 may be sufficient to cover the target area 200 at the pancreas 202 without further moving the transducer 50. In other cases, the transducer 50 may be further positioned (e.g., translated along, and/or rotated about, the longitudinal axis of the second elongated member 40) to thereby cover the entire target area 200. In some embodiments, the movement of the transducer 50 may be accomplished by moving the second elongated member 40 while energy is being delivered to thereby sweep the energy. Alternatively, the movement of the transducer 50 may be accomplished by moving the second elongated member 40 when the transducer 50 is not delivering any energy (e.g., between deliveries of energy).

In other embodiments in which multiple transducers 50 are provided at the device 10, the sweeping of the energy may not be required. For example, if there are multiple transducers 50 aligned along the axial length of the second elongated member 40 (like that shown in FIG. 2A), then one or more of the transducers 50 may be selectively activated to cover the longitudinal length of the target area 200. On the other hand, if the series of transducers 50 is not sufficient to cover the entire longitudinal length of the target area 200, the second elongated member 40 may be translated to move the transducers 50 so that energy from the transducers 50 can cover the entire longitudinal length of the target area 200.

As another example, if there are multiple transducers 50 disposed circumferentially around the longitudinal axis of the second elongated member 40 (like that shown in FIG. 2B), then one or more of the transducers 50 may be selectively activated to cover the transverse width of the target area 200. On the other hand, if the transducers 50 are not sufficient to cover the entire transverse width of the target area 200, the second elongated member may be rotated to move the transducers 50 so that energy from the transducers 50 can cover the entire transverse width of the target area 200.

In some embodiments, if the transducers 50 are arranged in an array configuration (like that shown in FIG. 2C), then the phasing of the transducers 50 may be controlled to thereby aim a focal point of the ultrasonic energy to different positions in the target area 200. The focal point may be sequentially placed at the different positions until the entire volume of the target area 200 has been treated.

In the illustrated example, the securing mechanism 30 is a balloon, which may also be used to couple ultrasonic energy to target area 200. When the transducer(s) 50 are activated, ultrasonic energy is emitted through the balloon 30 to treat target area 200 in the pancreas 202.

During the treatment process, the thermal imaging device 90 may be used to monitor the extent of heating of the target tissue and adjacent tissues. The purposes of the thermal imaging guidance are to assure complete ablation of targeted tumor tissue while minimizing damage to adjacent normal structures. In some embodiments, the thermal imaging device 90 may be configured to provide a map showing an extent of the heated areas. The map may be presented in different colors to show the different values of temperature at different locations. In some embodiments, the map may be displayed together with (e.g., superimposed over) an anatomy image, and may be presented to the user of the device 10 so that the user can see the extent of the heating relative to the anatomical features. In some embodiments, the user, from looking at the map, may determine that the target area 200 has not been sufficiently treated. This may occur, for example, when part(s) of the target area 200 has not received any energy from the transducer(s) 50, or when part(s) of the target area 200 has not received a sufficient amount of energy to kill off the tumor cells. In such cases, the user may reposition the transducer(s) 50, select another one of the transducer(s) 50 for activation, and/or change an operation parameter (e.g., power level, phase, etc.) for the transducer(s) 50, to thereby deliver energy to the untreated or under-treated areas.

After the procedure is completed, the fluid in the securing mechanism 30 is extracted to enable removal of the device 10 from the patient's body.

Figure 4A:
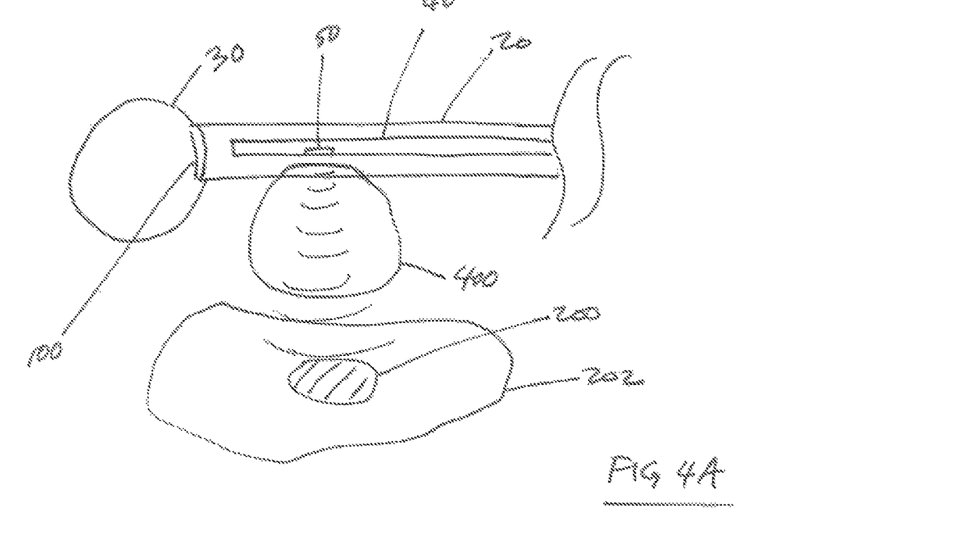
FIG. 4A-4E illustrate alternative embodiments of the device of FIG. 1A.

FIG. 4A shows a variation of the device 10 of FIG. 1A. The device 10 of FIG. 4A is the same as that in FIG. 1A, except that the securing mechanism 30 is located at the distal tip of the first elongated member 20, instead of the securing mechanism 30 extending from the side of the first elongated member 20. In this embodiment, the device 10 includes an energy coupling balloon 400 at the distal end 100 of the first elongated member 20 for coupling energy from the transducer(s) 50 to target area 200 in the pancreas 202. Both the securing mechanism 30 and balloon 400 may have an un-expanded (e.g., un-infalted) configuration so that they assume a low profile for delivery through the mouth to the target site 200. In some embodiments, the securing mechanism 30 may be a balloon. In such cases, when the balloons 30, 400 reach the treatment site, fluid is delivered to expand the balloons 30, 400. The expanded balloon 30 functions as an anchor to secure the distal end 100 of the first elongated member 20 relative to the wall of the stomach or the duodenum 300, and the expanded balloon 400 is used to couple energy from the transducer(s) 50 to the target area 200.

Figure 4B:
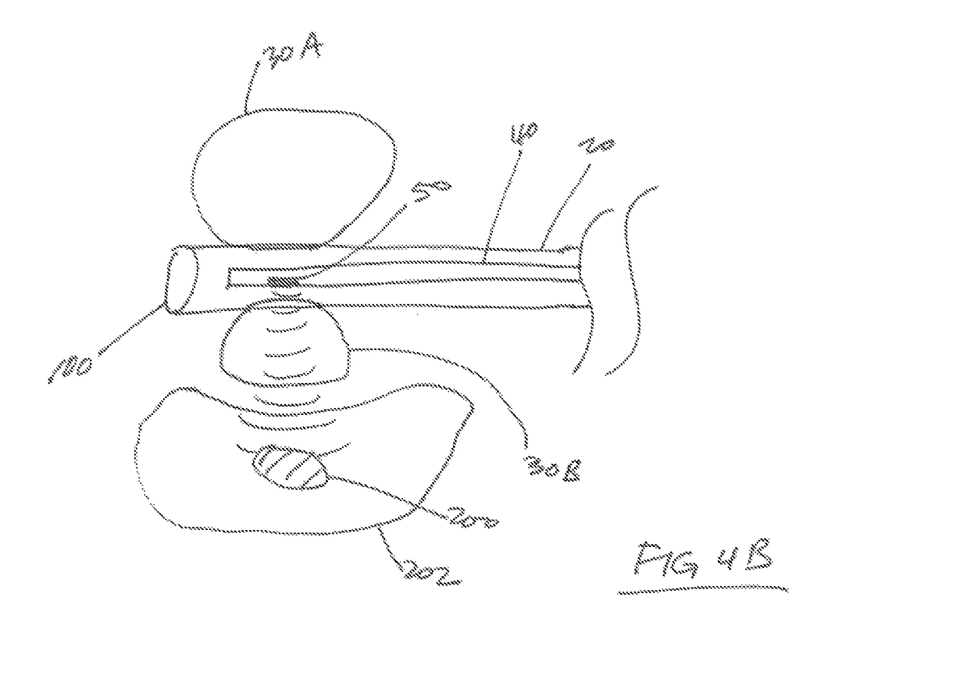

In other embodiments, the device 10 may have two balloons 30A and 30B (FIG. 4B). Balloons 30A and 30B function together for anchoring, but balloon 30B may also be used for coupling energy to the target area 200. In such embodiments, balloon 30A is more expandable than 30B, thereby allowing the balloon 30A to fit different patient sizes. In some embodiments, the device may have respective delivery channels for delivering fluid to the respective balloons 30A, 30B. In such cases, the amount of fluid in each of the balloons 30A, 30B may be selectively adjusted. In other embodiments, the balloons 30A, 30B may be in fluid communication with each other. In such cases, the balloons 30A, 30B may be expanded together using a same fluid source. When the energy coupling balloon 30B has reached a desired size, the energy coupling balloon 30B will stop expanding, and the balloon 30A may be continued to expand by delivering additional fluid until the balloon 30A has reached a desired size sufficient to anchor the device at the treatment site.

Figure 4C:
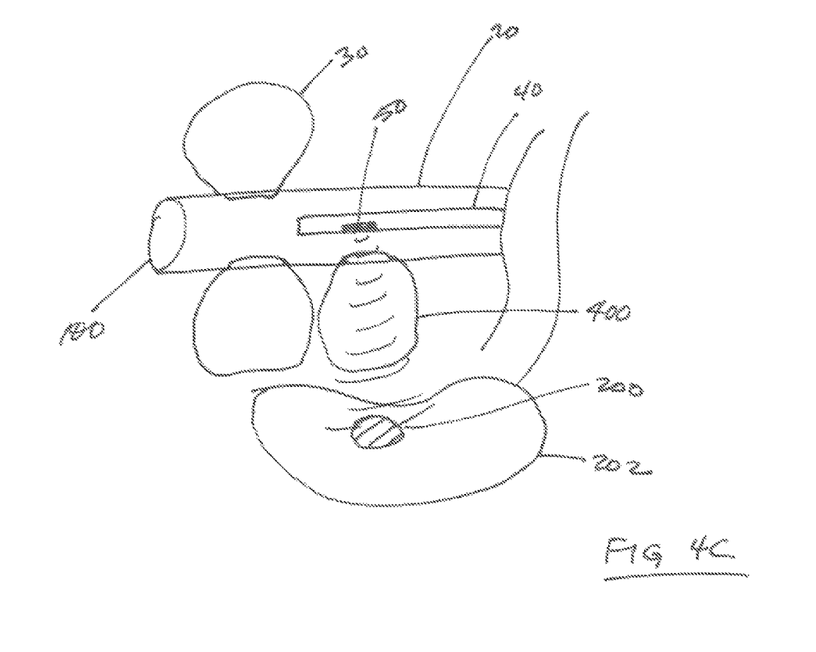

In other embodiments, the device 10 may have a balloon dedicated for coupling ultrasonic energy. For example, in other embodiments, the device 10 may have an energy coupling balloon 400 for coupling ultrasonic energy from the transducer(s) 50 to the target area 200 at the pancreas 202 (FIG. 4C). The device 10 is the same as the one shown in FIG. 1A, except that the device 10 has the additional balloon 400 for coupling ultrasonic energy. In such embodiments, the balloon 400 is operated the same way as balloon 400 described with reference to FIG. 4A.

Figure 4D:
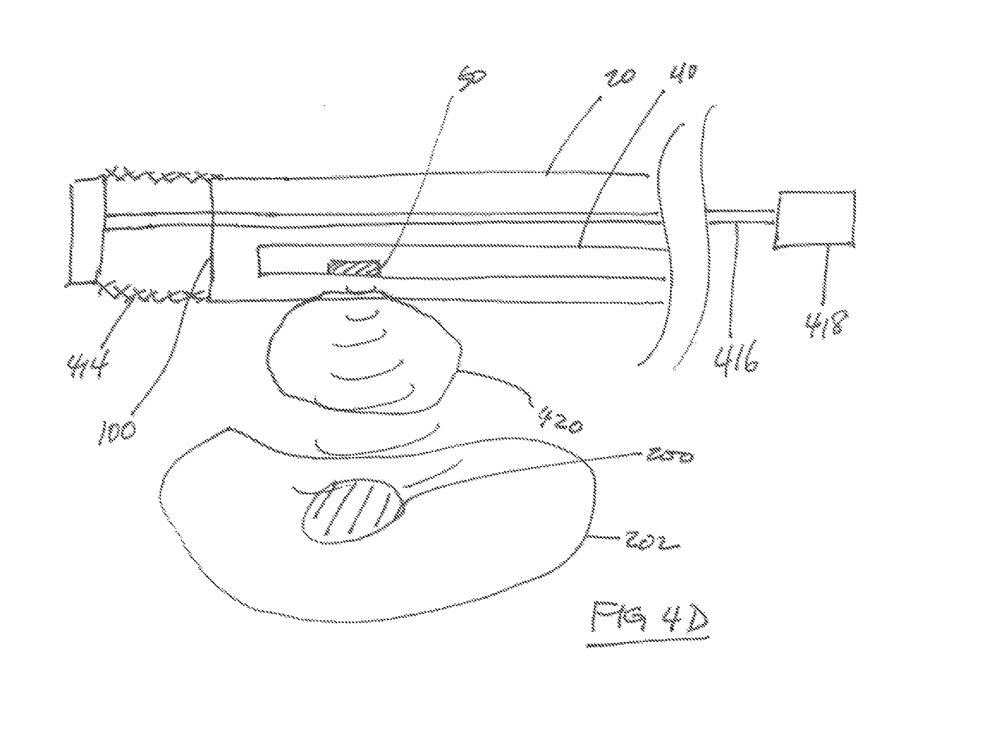

FIG. 4D shows a variation of the device 10 of FIG. 1A. The device 10 of FIG. 4D is the same as FIG. 1A, except that the securing mechanism 30 is a structural mesh 414. The structural mesh 414 may be in a collapsed configuration allowing it to be delivered into a patient. The structural mesh 414 includes a distal end that is coupled to a rod 416, and a proximal end that is coupled to the first elongated member 20. The rod 416 is coupled to a handle 418, that may be used to pull the rod 416 backward relative to the first elongate member 20 to expand the mesh 414, or may be used to push the rod 416 forward relative to the first elongate member 20 to collapse the mesh 414. When the structural mesh 414 reaches the treatment site, the mesh 414 is expanded to engage tissue at the treatment site. The expanded mesh 414 may have a size that is sufficiently large, so that the expanded mesh can engage with, and press against, the wall of the stomach or the duodenum, thereby allowing the mesh 414 to function as an anchor to secure the distal end 100 of the first elongated member 20 relative to the wall of the stomach or the duodenum. In the illustrated embodiments, the device 10 includes an energy coupling balloon 400 similar to the ones shown in FIGS. 4A and 4C for coupling energy to the target area 200.

Figure 4E:
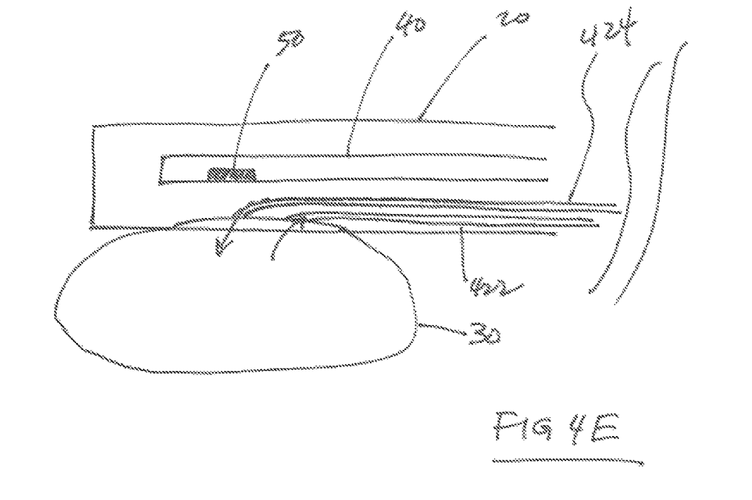

In one or more embodiments described herein, in which the device 10 includes an energy coupling balloon, fluid in such energy coupling balloon may be circulated to thereby provide a cooling effect during a treatment procedure. For example, as shown in FIG. 4E, in some embodiments in which the balloon 30 is used for coupling energy from the transducer(s) 50 to target area, circulating fluid may be used to fill the balloon. The circulating water functions to prevent tissue damage (at the stomach wall or the duodenum that is in contact with the balloon 30) when energy is transmitted from the transducer(s) 50 through the balloon to the target area. In some embodiments, the circulating fluid may also cool the transducer(s) 50. In the illustrated figure, one channel 422 may be used to extract the heated fluid (resulted from delivery of energy from the transducer(s) 50) from the balloon 30 and another channel 424 may be used to deliver cooling fluid to the balloon 30. The channel 422 may be located in a wall of the first elongated member 20, or alternatively, be implemented using a tube. Similarly, the channel 424 may be located in a wall of the first elongated member 20, or alternatively, be implemented using a tube.

Figure 5:
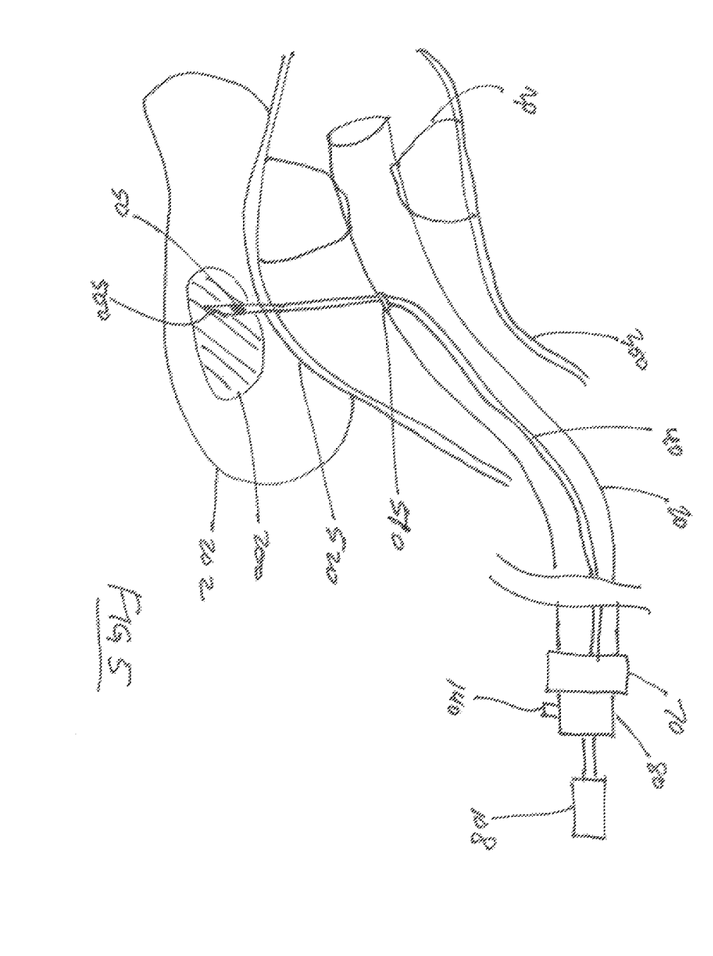
FIG. 5 illustrates an alternative embodiment of the device of FIG. 1A.

In the above embodiments, energy from the transducer(s) 50 is delivered through a wall of the stomach or the duodenum to reach target area at the pancreas. In other embodiments, energy from the transducer(s) 50 may be delivered from within the pancreas. FIG. 5 shows a variation of the device 10 in which the second elongated member 40 may be moved out of the first elongated member 20 to place the transducer(s) 50 at the pancreas. In the illustrated embodiments, the first elongated member 20 has an opening 510 for allowing the second elongated member 40 exit therethrough, and the second elongated member 40 has a sharp distal tip 500. During a treatment procedure, the second elongated member 40 is inserted into the first elongated member 20 and through the esophagus to the stomach or duodenum 300. Once the second elongated member 40 reaches a desirable position within the stomach or duodenum 300, it is then pushed out of the first elongated member 20 through the opening 510 at the side wall of the first elongated member 20. The sharp distal tip 500 of the second elongated member 40 punctures through the stomach or duodenum wall 520, and into the pancreas until the transducer(s) 50 reach a desired position in the target area 200. In some embodiments, the distal end of the second elongated member 40 may be steerable to thereby allow the distal end of the second elongated member 40 to be steered to a desired direction for advancing the second elongated member 40. After the transducer(s) 50 has been desirably positioned, the transducer(s) 50 may then be activated (by using the control 140) to deliver ultrasonic energy from within the pancreas 202 to treat the target area 200 in the pancreas 202. In the illustrated embodiments, the transducer(s) 50 may be configured to deliver energy radially away from the axis of the second elongated member 40. As similarly discussed, the treatment may be guided by a thermal imaging device 90 to monitor the extent of the heating of the target tissue.

As discussed, the transducer(s) 50 in the device 10 of FIG. 5 is configured to deliver ultrasonic energy radially away from the second elongated member 40. In some embodiments, the transducer(s) 50 may be disposed circumferentially around the second elongated member 40 to form a ring configuration. This configuration allows energy to be delivered over a circumferential range of 360°. In other embodiments, the transducer(s) 50 may be disposed over a partial circumference of the second elongated member 40. Also, in some embodiments, the device 10 of FIG. 5 may have a single transducer 50 (like that shown in the device 10 of FIG. 1A). In other embodiments, the device 10 of FIG. 5 may have multiple transducers 50. For example, the device 10 of FIG. 5 may have transducers 50 arranged in manners shown in FIG. 2A, FIG. 2B, or FIG. 2C. The control 140 may be used to selectively activate one or more of the transducers 50, and/or to control operation parameter(s) (such as, power level, phase, activation duration, etc.) for the transducers 50.

Also, in some embodiments, the transducer(s) 50 inside the pancreas may be positioned by moving the second elongated member 40 to thereby aim an energy delivery path of the transducer(s) 50 towards a desired direction, as similarly discussed. For example, in some embodiments, the second elongated member 40 may be advanced distally or retracted proximally to thereby change the position of the transducer(s) 50 along an axis of the second elongated member 40. Alternatively, or additionally, the second elongated member 40 may also be rotated about its axis to turn the transducer(s) 50 so that they face a certain direction.

In other embodiments, instead of delivering ultrasonic energy, the component(s) 50 may be other types of energy delivery component(s). For example, in other embodiments, the energy delivery component(s) 50 at the device 10 of FIG. 5 may be configured to deliver radiofrequency energy, electrical energy, radiation, or any of other types of energy for treating the target area 200.

Figure 6:
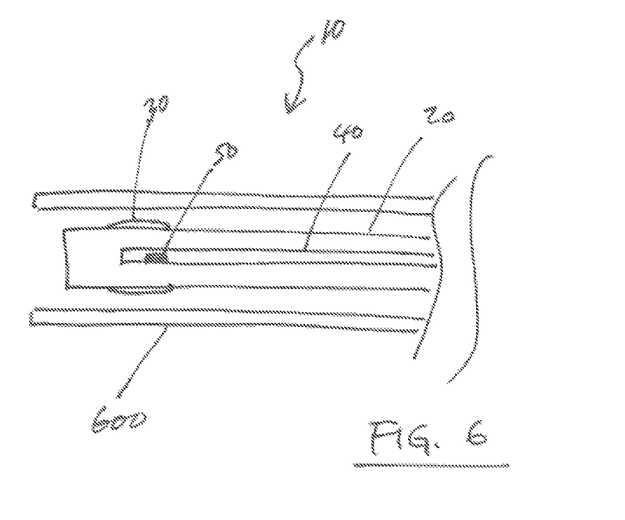
FIG. 6 illustrates an alternative embodiment of the device of FIG. 1A.

In one or more embodiments described herein, the device 10 may optionally further include a delivery tube for housing the first elongated member 20 and the second elongated member 40. FIG. 6 shows a delivery tube 600 that may be used to house the first elongated member 20 and the second elongated member 40. During use, the securing mechanism 30 at the first elongated member 20 is confined within the lumen of the delivery tube 600. The delivery tube 600 is inserted into the patient until the distal end of the delivery tube 600 reaches a treatment site. The first elongated member together with the securing mechanism 30 is then deployed out of the distal opening at the delivery tube 600.

Figure 7:
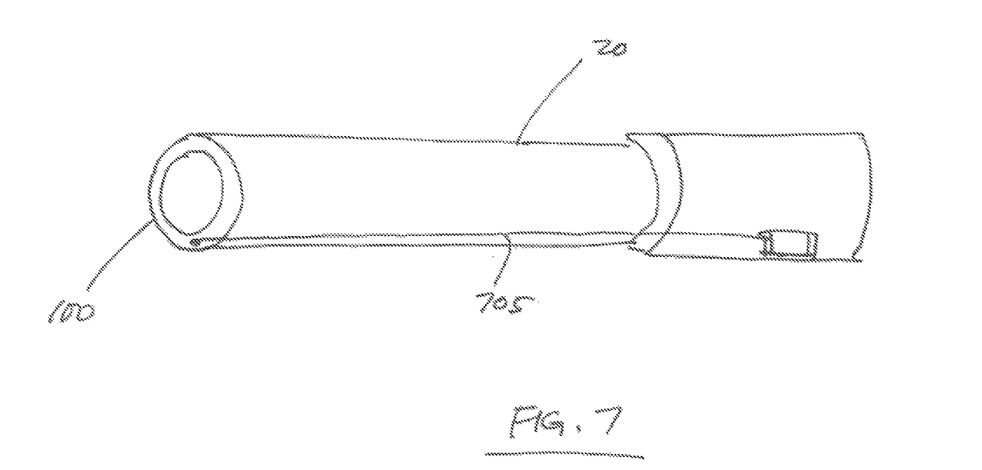
FIG. 7 illustrates an alternative embodiment of the device of FIG. 1A.

As shown in FIG. 7, the device 10 may optionally also include a steering mechanism for bending the distal end 100 of the first elongated member 20. For example, one or more steering wires 705 may be coupled to the distal end 100 that bend the first elongated member 20 in response to tension applied at the proximal end of the steering wire(s).

In the above embodiments, the device 10 has been described as having, or being used with, a thermal imaging device 90. In some embodiments, instead of a thermal imaging device, the component 90 may be a thermal couple or other temperature sensing device for monitoring the extent of heating at the target area. Also, in other embodiments, the component 90 may be other types of sensor configured to sense other characteristics associated with a heating of tissue. The component 90 may be a part of the device 10, or alternatively be used with the device 10.

In the above embodiments, the device 10 has been described as being configured/used to deliver ultrasonic energy to heat tissue(s). In other embodiments, the device 10 may be configured/used to apply ultrasonic energy for drug activation and targeting. For example, a drug may be consumed by a patient, or may be administered to within a patient (e.g., using a needle or IV). Then the device 10 may be inserted into the patient in the manner described herein, and may be operated to deliver ultrasonic energy to activate the drug inside the patient. In further embodiments, the device 10 may be configured/used to apply ultrasonic energy to generate hyperthermia at tissue within the patient. Thus, the device 10 may be configured to perform thermal therapy. As used in this specification, the term "thermal therapy" is not limited to delivering/creating heat at tissue, and may refer to delivering/creating hyperthermia at tissue. Similarly, the term "ultrasonic energy" or "energy" is not limited to energy for creating heat (ablation), and may be energy for creating hyperthermia. In still further embodiments, the device 10 may be configured/used to apply ultrasonic energy to generate a biological/physiological effect, such as tissue remodeling. In other embodiments, the device 10 may be configured/used to apply ultrasonic energy to create mechanical effect(s) in target tissue(s). The energy can be delivered before, simultaneous, or after drug is infused or placed in the body.

Also, in other embodiments, instead of delivering ultrasonic energy, the component(s) 50 may be other types of energy delivery component(s). For example, in other embodiments, the energy delivery component(s) 50 at the device 10 of FIGS. 1-4 may be configured to deliver radiofrequency energy, electrical energy, radiation, or any of other types of energy for treating the target area 200.

Although particular embodiments have been shown and described, it will be understood that it is not intended to limit the claimed inventions to the preferred embodiments, and it will be obvious to those skilled in the art that various changes and modifications may be made without departing from the spirit and scope of the claimed inventions. The specification and drawings are, accordingly, to be regarded in an illustrative rather than restrictive sense. The claimed inventions are intended to cover alternatives, modifications, and equivalents.

The invention claimed is:

1. A method of treating pancreatic cancer in a patient, comprising:
   inserting a device into a stomach or a duodenum, wherein the device comprises a first elongated member with a lumen, and a second elongated member disposed within the lumen of the first elongated member, the second elongated member comprising a transducer for providing ultrasonic energy;
   securing at least a portion of the device in position relative to the stomach or the duodenum, wherein the at least a portion of the device comprises an expandable member, and the act of securing the at least a portion of the device comprises expanding the expanding member to engage at least two opposite walls of the stomach or the duodenum;
   moving the second elongated member relative to the first elongated member, wherein the act of moving the second elongated member comprises translating the second elongated member relative to the first elongated member;
   inserting the transducer through a wall of the stomach or through a wall of the duodenum into a pancreas; and
   delivering the ultrasonic energy from the transducer to treat a target site in the pancreas;
   wherein the ultrasonic energy is delivered from within the pancreas to directly interact with tissue in the pancreas to cause a change at a cellular level of the tissue;
   wherein the transducer comprises a plurality of transducer elements that are arranged at the second elongated member, wherein the act of delivering the ultrasonic energy comprises activating at least one of the plurality of the transducer elements that aligns with the target site to deliver the ultrasonic energy to the target site in the pancreas, while one or more other ones of the transducer elements not aligned with the target site are un-activated, the at least one of the plurality of the transducer elements constitute a subset, and not all, of the transducer elements.

2. The method of claim 1, wherein the ultrasonic energy is delivered from the device to create heat, hyperthermia, or thermal ablation, at the target site.

3. The method of claim 1, the ultrasonic energy is delivered to create mechanical perturbations at the target site in the pancreas.

4. A method of treating pancreatic cancer in a patient, comprising:
　inserting a device into a stomach or a duodenum;
　securing at least a portion of the device in position relative to the stomach or the duodenum; and
　delivering ultrasonic energy from the device to treat a target site in a pancreas;
　wherein the at least a portion of the device comprises an expandable member, and the act of securing the at least a portion of the device comprises expanding the expanding member to engage at least two opposite walls of the stomach or the duodenum;
　wherein the device further comprises a first elongated member with a lumen, and a second elongated member disposed within the lumen of the first elongated member, the second elongated member comprising an energy source for providing the ultrasonic energy to treat the target site, wherein the first elongated member is configured to house the expandable member, and wherein the method further comprises moving the second elongated member relative to the first elongated member, wherein the act of moving the second elongated member comprises translating the second elongated member relative to the first elongated member; and
　wherein the energy source comprises a plurality of transducer elements that are arranged at the second elongated member, wherein the act of delivering the ultrasonic energy comprises activating at least one of the plurality of the transducer elements that aligns with the target site to deliver the ultrasonic enemy to the target site in the pancreas, while one or more other ones of the transducer elements not aligned with the target site are un-activated, the at least one of the plurality of the transducer elements constitute a subset, and not all, of the transducer elements.

5. The method of claim 4, wherein the ultrasonic energy is delivered through a wall of the stomach or through a wall of the duodenum.

6. The method of claim 4, wherein the expandable member comprises a stomach balloon or a duodenum balloon.

7. The method of claim 4, wherein the expandable member comprises a balloon, and the ultrasonic energy is delivered through the balloon.

8. The method of claim 4, wherein the device further comprises a balloon outside the expandable member.

9. The method of claim 4, further comprising monitoring a thermal therapy process for the target site using a sensor that senses a characteristic of the target site.

10. A device for treating pancreatic cancer in a patient, comprising:
　a first elongated member with a lumen, the first elongated member configured for insertion into a stomach or a duodenum;
　a second elongated member disposed within the lumen of the first elongated member, the second elongated member comprising an energy source for providing ultrasonic energy, and an expandable member, the expandable member being a stomach balloon configured to secure at least a portion of the device relative to the stomach, or a duodenum balloon configured to secure the at least a portion of the device relative to the duodenum;
　wherein the second elongated member has an exterior portion for contacting tissue, and is configured for translation and/or rotation relative to the first elongated member;
　wherein the energy source is configured to deliver the ultrasonic energy to treat a target site in the pancreas; and
　wherein the energy source comprises a plurality of transducer elements that are arranged at the second elongated member, wherein the second elongated member is moveable to align one or more of the transducer elements with the target site, and wherein at least one of the plurality of the transducer elements that aligns with the target site is configured to deliver the ultrasonic energy to the target site in the pancreas, while one or more other ones of the transducer elements not aligned with the target site are configured to be un-activated, the at least one of the plurality of the transducer elements constitute a subset, and not all, of the transducer elements.

11. The device of claim 10, wherein the transducer elements are along a longitudinal axis of the device.

12. The device of claim 10, wherein the transducer elements are along a circumference of the device.

13. The device of claim 10, further comprising a user interface that allows a user to selectively activate one or more of the transducer elements, and/or to adjust an amount of energy being delivered by the one or more of the transducer elements.

14. A device for treating pancreatic cancer, comprising:
　a first elongated member with a lumen, the first elongated member configured for insertion into a stomach or a duodenum;
　an expandable member coupled to the first elongated member, wherein the expandable member is configured to engage at least two opposite walls of a stomach to secure at least a portion of the device relative to the stomach, or to engage at least two opposite walls of a duodenum to secure the at least a portion of the device relative to the duodenum, when in an expanded configuration;
　a second elongated member disposed within the lumen of the first elongated member, wherein the second elongated member is configured to translate relative to the first elongated member; and
　an energy source coupled to the second elongated member, the energy source configured to provide ultrasonic energy to treat a target site at a pancreas;
　wherein the second elongated member has a distal end configured to exit from within the lumen of the first elongated member radially away from a longitudinal axis of the first elongated member; and
　wherein the energy source comprises a plurality of transducer elements that are arranged at the second elongated member, wherein the second elongated member is moveable to align one or more of the transducer elements with the target site, and wherein at least one of the plurality of the transducer elements that aligns with the target site is configured to deliver the ultrasonic energy to the target site in the pancreas, while one or more other ones of the transducer elements not aligned with the target site are configured to be un-activated, the at least one of the plurality of the transducer elements constitute a subset, and not all, of the transducer elements.

15. The device of claim 14, further comprising a monitoring device configured to monitor a treatment progress while the energy source delivers the ultrasonic energy, the monitoring device comprising a sensor.

16. The device of claim 14, wherein the expandable member is distal to the first elongated member.

17. The device of claim 14, wherein the distal end of the second elongated member is configured to pierce into tissue at the target site.

* * * * *